United States Patent
Benni

(10) Patent No.: US 9,913,601 B2
(45) Date of Patent: Mar. 13, 2018

(54) METHOD AND APPARATUS FOR MONITORING A BLOOD OXYGEN SATURATION LEVEL RELATIVE TO A SATURATION THRESHOLD VALUE

(71) Applicant: CAS Medical Systems, Inc., Branford, CT (US)

(72) Inventor: Paul B. Benni, Acton, CT (US)

(73) Assignee: CAS Medical Systems, Inc., Branford, CT (US)

( * ) Notice: Subject to any disclaimer, the term of this patent is extended or adjusted under 35 U.S.C. 154(b) by 865 days.

(21) Appl. No.: 13/758,511

(22) Filed: Feb. 4, 2013

(65) Prior Publication Data

US 2013/0204105 A1 Aug. 8, 2013

Related U.S. Application Data

(60) Provisional application No. 61/594,752, filed on Feb. 3, 2012.

(51) Int. Cl.
*A61B 5/1455* (2006.01)
*A61B 5/00* (2006.01)

(52) U.S. Cl.
CPC ...... *A61B 5/14551* (2013.01); *A61B 5/14553* (2013.01); *A61B 5/7275* (2013.01); *A61B 5/7282* (2013.01); *A61B 5/746* (2013.01); *A61B 5/743* (2013.01)

(58) Field of Classification Search
CPC .................................................. A61B 5/1455
See application file for complete search history.

(56) References Cited

U.S. PATENT DOCUMENTS

| | | | |
|---|---|---|---|
| 6,456,862 B2 | 9/2002 | Benni | |
| 7,072,701 B2 | 7/2006 | Chen et al. | |
| 7,123,950 B2* | 10/2006 | Mannheimer | A61B 5/02455 600/300 |
| 8,078,250 B2 | 12/2011 | Chen et al. | |
| 2003/0088163 A1* | 5/2003 | Soller | 600/322 |
| 2008/0015424 A1* | 1/2008 | Bernreuter | 600/323 |
| 2008/0300474 A1 | 12/2008 | Benni | |
| 2009/0182209 A1 | 7/2009 | Benni | |

(Continued)

FOREIGN PATENT DOCUMENTS

WO 2012109661 8/2012

OTHER PUBLICATIONS

Fischer et al. "Noninvasive Cerebral Oxygenation May Predict Outcome in Patients Undergoing Aortic Arch Surgery", Journal of Thoracic and Cardiovascular Surgery, vol. 141, No. 3, Jun. 25, 2010.

*Primary Examiner* — Eric Winakur
*Assistant Examiner* — Marjan Fardanesh
(74) *Attorney, Agent, or Firm* — O'Shea Getz P.C.

(57) ABSTRACT

A method and apparatus for monitoring a blood oxygen saturation level within a subject's tissue is provided. The method includes the steps of: a) sensing the subject's tissue using a near infrared spectrophotometric oximeter, and producing a value representative of the oxygen saturation level within the sensed tissue; b) comparing the determined saturation value to a predetermined threshold oxygen saturation value; and c) determining at least one of a time under threshold (TUT) value or an area under threshold (AUT) value using the determined saturation value and the threshold value.

14 Claims, 2 Drawing Sheets

(56) References Cited

U.S. PATENT DOCUMENTS

| | | |
|---|---|---|
| 2009/0281403 A1 | 11/2009 | Benni |
| 2010/0049018 A1 | 2/2010 | Duffy et al. |
| 2010/0105998 A1 | 4/2010 | Benni |
| 2011/0237910 A1 | 9/2011 | Gamelin et al. |
| 2012/0271130 A1 | 10/2012 | Benni |

* cited by examiner

METHOD AND APPARATUS FOR MONITORING A BLOOD OXYGEN SATURATION LEVEL RELATIVE TO A SATURATION THRESHOLD VALUE

Applicant hereby claims priority benefits under 35 U.S.C. § 119(e) of U.S. Provisional Patent Application No. 61/594,752 filed Feb. 3, 2012, the disclosure of which is herein incorporated by reference.

BACKGROUND OF THE INVENTION

1. Technical Field

This invention relates to methods for non-invasively determining biological tissue oxygenation in general, and to non-invasive methods utilizing near-infrared spectroscopy (NIRS) techniques for determining the same in particular.

2. Background Information

Methods and apparatus for determining the oxygen saturation value ("$StO_2$") of the tissue of a subject are frequently used to monitor subjects before, during and after surgical procedure, and/or to monitor subjects at risk of tissue oxygen deprivation; e.g., neonates, elderly subjects, etc. Although these devices, and in particular those devices that utilize near-infrared spectroscopy (NIRS) techniques, provide valuable information, it would be of great clinical value to produce additional data having clinical relevance.

DISCLOSURE OF THE INVENTION

According to an aspect of the present invention, a method for monitoring a blood oxygen saturation level within a subject's tissue is provided. The method includes the steps of: a) sensing the subject's tissue using a near infrared spectrophotometric oximeter, and producing a value representative of the oxygen saturation level within the sensed tissue; b) comparing the determined saturation value to a predetermined threshold oxygen saturation value; and c) determining at least one of a time under threshold (TUT) value or an area under threshold (AUT) value using the determined saturation value and the threshold value.

According to another aspect of the present invention, an apparatus for monitoring a blood oxygen saturation level within a subject's tissue is provided. The apparatus includes one or more sensors and an analyzer. Each sensor has one or more light sources and one or more light detectors. The analyzer has a processor, and the analyzer is in communication with the one or more sensors. The processor is operable to control the one or more sensors to sense the subject's tissue, and produce a value representative of the oxygen saturation level within the sensed tissue, and to compare the determined saturation value to a predetermined threshold oxygen saturation value, and to determine at least one of a time under threshold (TUT) value or an area under threshold (AUT) value using the determined saturation value and the threshold value.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

DETAILED DESCRIPTION THE INVENTION

The present invention relates to methods and apparatus for non-invasively and spectrophotometrically determining the blood oxygen saturation level within a subject's tissue. The present method may be implemented, for example, in the form of the present apparatus which includes one or more sensors capable of transmitting a light signal into the tissue of a subject and sensing the light signal once it has passed through the tissue via transmittance or reflectance, and an analyzer. As will be described below, the present apparatus is a near infrared spectrophotometric (NIRS) type oximeter adapted in the manner described below.

Figure 1:
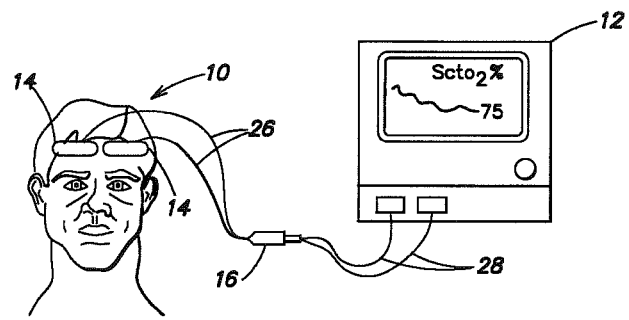
FIG. 1 is a diagrammatic representation of a spectrophotometric NIRS oximeter.
Figure 2:
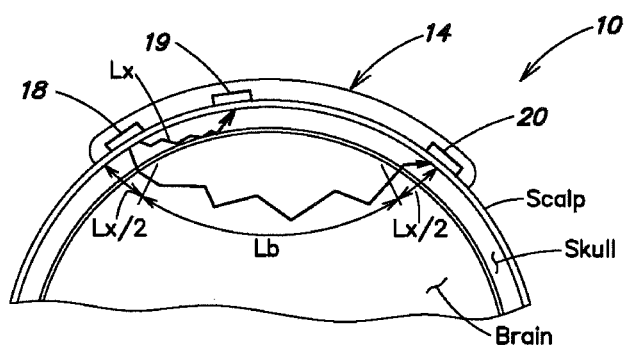
FIG. 2 is a diagrammatic representation of a sensor placed on a subject's head.
Figure 3:
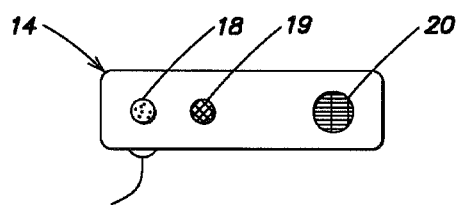
FIG. 3 is a diagrammatic view of a NIRS sensor.

Referring to FIGS. 1-3, an example of an acceptable NIRS type oximeter includes at least one sensor 10 in communication with the analyzer 12. The sensor 10 is typically a flexible structure that can be attached directly to a subject's body, and includes one or more light sources 14 and one or more light detectors 16, 18. The light sources 14 selectively emit light signals of known but different wavelengths. The light sources 14 may, for example, be light emitting diodes (LEDs) and the light detectors 16, 18 may, for example, be photodiodes. In the embodiment shown in FIG. 1, the sensor 10 includes connector cables 20 that allow communication (e.g., electrical, optical, etc) between the sensor 10 and the analyzer 12. Examples of acceptable NIRS sensors are described in U.S. patent application Ser. Nos. 13/444,509; 13/070,172; 12/607,648; 12/514,955; 12/090,671; and 12/096,132, and PCT Patent Application Serial No. PCT/US12/24889, all of which are commonly assigned to the assignee of the present application and each of which is hereby incorporated by reference in its entirety.

The analyzer 12 includes a processor 22 for providing signals to, and processing signals from, the sensor 10 (e.g., light intensity signals associated with the light sources 14 and the light detectors 19, 20) in the manner described herein, a display (e.g., an LED screen), and an input device (e.g., a keypad or touch screen). A person of skill in the art will recognize that the processor 22 may assume various forms (e.g., digital signal processor, analog device, etc.) capable of performing the functions described herein. The processor 22 may be adapted to use a variety of algorithms for sensing the subject's tissue and determining the oxygen saturation value ("$StO_2$") of the interrogated tissue. Consequently, the processor 22 is not limited to using any particular algorithm (or the methodology reflected in the algorithm) for determining $StO_2$ values. Examples of acceptable algorithms for determining $StO_2$ values are described in U.S. Pat. Nos. 6,456,862; 7,072,701; and 8,078,250, and U.S. Patent Publication No. 2009/0281403, all of which are commonly assigned with the present application, and each of which is hereby incorporated by reference in its entirety. As stated above, however, the present invention is not limited to use with any particular algorithm for determining a $StO_2$ value.

Figure 4:
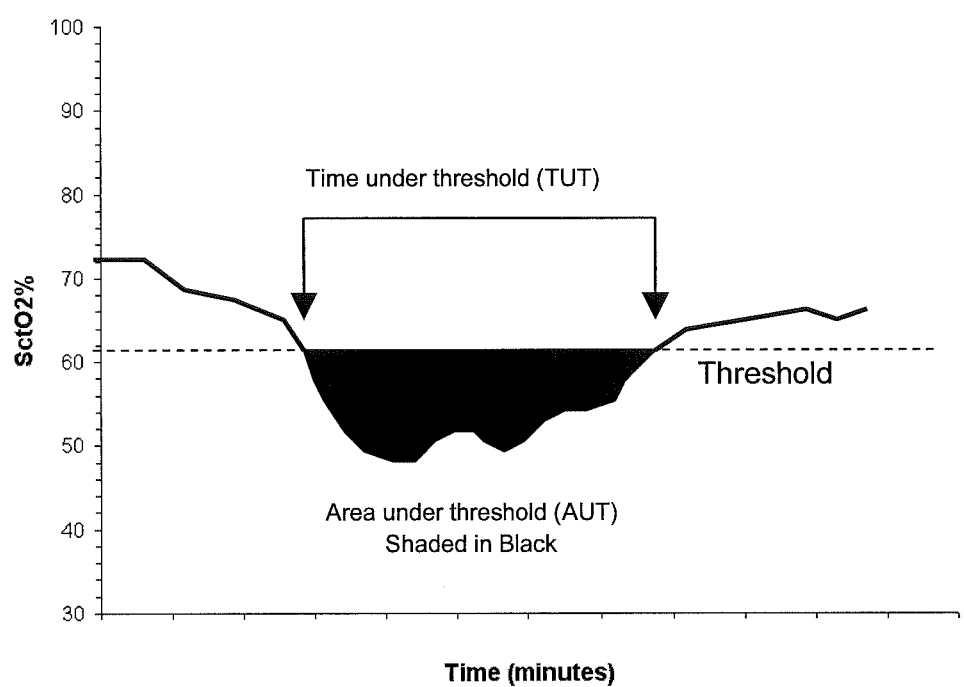
FIG. 4 is a graph of $StO_2$ versus time, illustrating TUT and AUT.

Referring to FIG. 4, according to the present invention the processor 22 is adapted to determine time under threshold ("TUT") values and/or area under threshold ("AUT") values. A TUT value is representative of an amount of time that determined $StO_2$ values are below a $StO_2$ threshold (i.e., amount of time when $StO_2$ threshold>$StO_2$ value). An AUT value is representative of the magnitude of the difference between the threshold $StO_2$ value and the determined $StO_2$ as a function of the time period when the threshold $StO_2$ value is greater than the determined $StO_2$ value (i.e., $StO_2$ threshold–$StO_2$ value, when $StO_2$ threshold>$StO_2$ value). FIG. 4 depicts AUT and TUT on an axis graph of $StO_2$ values versus time.

A TUT value may be expressed in terms of the amount of time the determined $StO_2$ value is below the $StO_2$ threshold value during a given evaluation period. The TUT value can be expressed in various different units of measure (e.g., minutes, seconds), or expressed as a percentage, ratio, etc. For example, if during a one hour evaluation period, the subject's determined $StO_2$ level was below the threshold $StO_2$ value for fifteen minutes; the TUT value may be described as fifteen minutes, or may be described as a 25% TUT percentage, etc. In physiological terms, the TUT value represents the time duration of the subject's accumulated tissue oxygen deficit. For example, if the subject's $StO_2$ level drops below the threshold, subsequently rises above the threshold, and subsequently drops below the threshold again, the TUT value only accounts for the cumulative time that the subject's $StO_2$ level was below the threshold $StO_2$ value. If the processor 22 is adapted to determine a $StO_2$ value periodically (e.g., a sample rate period equal to every 2 seconds) then the processor 22 may be adapted to compare the determined $StO_2$ value to the threshold value after each sampling period. If the threshold $StO_2$ value is greater than the determined $StO_2$ value (i.e., $StO_2$ Threshold>$StO_2$ value), then the TUT value can be calculated, for example, as follows:

TUT(present cumulative value for evaluation period)
=TUT(past)+sample rate time period.

In this example, if there has previously been no sample period with a determined $StO_2$ value less than the threshold $StO_2$ value during the evaluation period, then the "TUT (past)" value would equal zero, and the "TUTpresent" value would equal the sample rate time period. On the other hand, if during the evaluation period there had previously been one or more sample periods with a determined $StO_2$ value less than the threshold $StO_2$ value, then the "TUT(past)" value would equal the cumulative time of the TUT sample periods, and the "TUTpresent" value would equal the sum of the "TUT(past)" value and the most recent sample rate time period. The above equation for determining a TUTpresent value is an example of an equation that can be used and the present invention is not limited thereto.

If the threshold $StO_2$ value is less than the determined $StO_2$ value, then the TUT value remains constant and TUT (present)=TUT(past).

The AUT value for an evaluation period (e.g. "AUTpresent") may be expressed as the sum of the individual AUT values determined for each sample rate period wherein the $StO_2$ threshold value is greater than the determined $StO_2$ value. The AUT value for a given sample period (in which the $StO_2$ threshold>$StO_2$ value), may be determined as the product of the difference between the threshold $StO_2$ value and the determined $StO_2$ value, and the duration of the sample rate period (i.e., StO2 Threshold–$StO_2$ value)× sample rate period). Like the TUT value, the AUT value can be expressed in various different units of measure (e.g., area), or expressed as a percentage, ratio, etc. In physiological terms, an AUT value represents the magnitude of accumulated tissue oxygen saturation deficit multiplied by time duration below threshold. For example, if the subject's $StO_2$ value drops below the threshold, subsequently rises above the threshold, and then subsequently drops below the threshold again, the cumulative AUT value represents only the periods in which the subject's determined $StO_2$ value is below the threshold $StO_2$ value. If the processor 22 is adapted to determine a $StO_2$ value periodically (e.g., a sample rate of every 2 seconds) then the processor 22 may be adapted to compare the determined $StO_2$ value to the threshold $StO_2$ value after each sampling period. If the threshold $StO_2$ value is greater than the determined $StO_2$ value (i.e., StO2 Threshold>StO2 value), then the AUT value can be calculated; e.g.:

AUT(present cumulative value for evaluation period)
=AUT(past)+(StO2 Threshold–StO2 value)×
sample rate period In this example, if there has been no sample period with a determined $StO_2$ value less than the threshold $StO_2$ value previously during the evaluation period, then the "AUT (past)" value would equal zero, and the "AUTpresent" value would equal the difference between the $StO_2$ threshold value and the $StO_2$ determined value times the sample rate time period of the most recent time period. On the other hand, if during the evaluation period there had previously been one or more sample periods with a determined $StO_2$ value less than the threshold $StO_2$ value, then the "AUT(past)" value would equal the sum of the product of each deficient sample rate period times the difference in $StO_2$ values for the respective time period, and the "AUTpresent" value would equal the sum of the "AUT(past)" value and the AUT value for the most recent sample rate time period. The above equation for determining an AUTpresent value is an example of an equation that can be used and the present invention is not limited thereto.

If the threshold $StO_2$ value is less than the determined $StO_2$ value, then the AUT value remains constant and AUT(present)=AUT(past).

Physiologically, the value of a $StO_2$ value being a quantitative magnitude of tissue oxygen saturation may be described as a one dimensional real-time physiological measurement. TUT, representing the amount of time during which a tissue oxygen deficit condition exists, may also be described as a one dimensional physiological measurement. In contrast to a $StO_2$ value determined at a particular point in time, however, a TUT value provides clinically relevant information relating to a tissue oxygen deficit condition as a function of time; e.g., a value indicative of how much time a tissue oxygen deficit condition existed over a given evaluation period. AUT, on the other hand, can be described as providing two dimensional information because it provides information relating to both the magnitude of the tissue oxygen deficit condition, and information relating to the temporal duration of the tissue oxygen deficit condition for a given evaluation period. Consequently, the user is provided with additional information that can be used in evaluating the subject.

The threshold $StO_2$ value may be selected in a variety of ways. For example, the analyzer 12 may be adjusted by the user (e.g., clinician, etc) to have a particular threshold value; e.g., the analyzer may acquire the threshold value via the user. Alternatively, the analyzer 12 may be adapted to select a threshold $StO_2$ value based on subject characteristics, which may be input into the device in a variety of different ways (e.g., manually, electronically, etc). The threshold $StO_2$ value may be selected based on one or more characteristics of the subject, including age, weight, height, gender, health, diagnosis, blood pressure, hematocrit, ethnicity, tobacco usage status (e.g., smoker or non-smoker), etc. The present invention is not limited to using these identified characteristics, and alternative characteristics that may influence the subject's $StO_2$ level may be used. The TUT and AUT values may be determined over one or more predetermined periods (e.g., minutes, hours, days, etc).

The present apparatus is further adapted to communicate at least one of the measured TUT value or the measured AUT value to the user. For example, embodiments of the apparatus may display AUT values and/or TUT values as a numeric value, or graphically (e.g., a graph similar to that shown in FIG. 4), or some combination thereof. The apparatus is not limited to any particular data display configuration.

In some embodiments, the present apparatus is adapted to evaluate at least one of the measured TUT value or the measured AUT value, to determine if an actionable oxygen desaturation condition exists, and to act (e.g., providing a user warning) if the actionable condition exists. The user may then choose a clinical intervention to increase tissue oxygen saturation or to minimize tissue oxygen desaturation episodes. The actionable oxygen dasaturation condition also can represent underlying physiological conditions such as deteriorating cardiac function and/or deteriorating circulatory dynamics that would result in reduced oxygen delivery to biological tissue or organs. Thus, the user will be alerted to review the subject being monitored physiological parameters to choose the best clinical intervention. The specific criteria (e.g., age, weight, gender, health, diagnosis, blood pressure, hematocrit, height, ethnic background, smoker, etc.) used as a factor in defining an actionable condition for the subject may vary depending upon the application at hand. For example, if the subject is above a predetermined age, unhealthy, has high blood pressure, and is a smoker, a duration and magnitude of AUT and/or TUT that may be clinically considered to be problematic for this subject may not be problematic at all for a subject who is below a predetermined age and healthy, is a non-smoker, and who has normal blood pressure. Alternatively, the criteria used to define an actionable condition may be arbitrarily chosen.

In some embodiments of the present invention, the AUT and/or TUT values may be determined as a function of time in predetermined evaluation periods (day 1, day 2, etc) or a moving time window (24 hours to present), thereby enabling a "trending" determination to determine the physiological health of the subject where $StO_2$ is measured. The comparison of AUT and/or TUT values may be between two time periods (e.g., T1, T2), or the comparison may be performed using a plurality of time periods. For example, the processor 22 may be adapted to:

1. Determine AUT1 and TUT1 for a first time period (e.g., Day 1) . . . .
2. Determine AUTn and TUTn for a "$n^{th}$" time period (e.g., Day "n"; where "n" is an integer greater than 1)
3. Display AUT and TUT values;

If the AUT and/or TUT values exhibit a decreasing trend over "n" periods of time, then the trending can be an indicator of improving physiological health. This is because tissue oxygen saturation is dropping less frequently in the most recent time period compared to a past time period which means the body's means to maintain adequate tissue oxygenation by physiological processes, such as (but not limited to) improved cardiac function and/or improved circulatory dynamics are occurring. Conversely, if the AUT and/or TUT values exhibit an increasing trend over "n" periods of time, then the trending can be an indicator of deteriorating physiological health. This is because tissue oxygen saturation is dropping more frequently in the most recent time period compared to a past time period which means the body's means to maintain adequate tissue oxygenation by physiological processes is deteriorating, such as (but not limited to) decreased cardiac function and/or decreased circulatory dynamics are occurring. The scope of the trending evaluation can be adjusted to suit the application at hand; e.g., the duration of the individual periods can be selected, and the collective evaluation period can be selected to suit the application at hand. The trending can also be evaluated using a moving time window.

In some embodiments, the processor 22 is adapted to determine a rate of change of AUT values and/or TUT values over a period of time. The rate of change can be the change of the AUT value and/or the TUT value between time periods or if a moving time window is used, the rate of change can be calculated and updated at any periodic time period that is less than the moving time window period. For example, if a 24 hour moving time window is used, the rate of change of AUT and TUT can be calculated every minute. The trending and/or rate of change information can be used by a user to determine the health of the subject.

In those embodiments wherein the present apparatus is adapted to evaluate at least one of the measured TUT value or the measured AUT value, to determine if an actionable oxygen desaturation condition exists, the analyzer may be adapted to make such evaluation over an evaluation time period. The analyzer may be adapted to make such evaluation using a determined rate of change of at least one of the AUT value or the TUT value, or both values. The analyzer may also be adapted to make such evaluation using a determined trend of the TUT values or the AUT values. Using examples to illustrate, an actionable condition may be determined using a TUT and/or an AUT value for a first time period, a TUT and/or an AUT value for a second time period, a TUT and/or an AUT value for a third time period, and so on for "n" time periods, where "n" is typically an integer value. It should be noted that the present invention is not limited to any particular number of periods. If the TUT and/or AUT values remain constant (e.g., values within a clinically acceptable data range) over the "n" periods, then no actionable oxygen desaturation condition is likely to exist, unless the TUT and/or AUT value was actionable to begin with. If the TUT and/or AUT values decrease during the "n" periods, then the subject's oxygen desaturation value is improving and here again, no actionable oxygen desaturation condition is likely to exist. On the other hand, if the AUT and/or TUT values increase during the "n" periods, then a trend of the increasing AUT and/or TUT values may be determined which can be used to determine the existence of an actionable oxygen desaturation condition. The determination of a trend can be particularly useful if the increases in AUT and/or TUT values are slight, or vary, from time period to time period, but the overall trend is an increase. The trend represents the AUT and/or TUT values as a function of time, and provides information that may not have been apparent looking at individual values. Similarly, if the AUT and/or TUT values increase during the "n" periods, then a rate of change of the increasing AUT or TUT values may be determined which can be used to determine the existence of an actionable oxygen desaturation condition. Here again, the rate of change represents the AUT and/or TUT values as a function of time, and provides information that may not have been apparent looking at individual values, possibly over less time than would be required to establish a trend. The examples given above are illustrated in terms of defined periods of time. A similar process can also be implemented during a moving time window; e.g., a trend or rate of change for the moving time window (e.g., 1 hour, 12 hours, 24 hours, etc time window). The trend and/or rate of change data in all these examples may be communicated to the user in a variety of different ways (e.g., a graphical plot) to facilitate the communication.

In some embodiments of the present invention, the analyzer 12 may be adapted to use AUT and/or TUT values to provide information that can be used as part of an intervention technique or therapy trigger in a highly dynamic physiological or clinical setting such as during cardiac surgery where clinical interventions are often predicated on transient changes in blood pressure, cardiac output, heart rate, etc. In this manner AUT and TUT values act as filters to transient desaturation events that may not necessarily need a triggered intervention. Using real-time AUT and TUT value calculations and selecting an AUT and TUT value for an intervention trigger, the user can provide an intervention to low tissue oxygen saturation value once the AUT and/or TUT intervention trigger is reached. As a result, unnecessary intervention can be avoided. As blood transfusion is a common intervention for low tissue oxygenation and other conditions, blood can be transfused only as needed since blood transfusions also carry certain risks that increase as more blood transfusions are performed. Performing blood transfusion based on transient physiological parameters (blood pressure, etc.) may result in unnecessary blood transfusions.

Conversely, AUT and TUT can be used in the above manner for preconditioning tissue to tolerate lower oxygenation levels. For each consecutive preconditioning therapy time period, it may be possible to increase the tolerance of the subject to higher levels of AUT and TUT. After preconditioning, when the body is subjected to a lower oxygen environment, the potential for tissue damage or dysfunction due to hypoxia and/or ischemia may be less. Also for athletic training, the ability of the muscle to work effectively through depletion of tissue oxygenation can be extended.

In some embodiments, the processor 22 may be adapted to determine AUT values and/or TUT values from two different measurement locations. If a sensor 10 is placed on the subject's forehead to measure cerebral $StO_2$, and a second sensor 10 placed on the flank (posterior abdominal region) to measure skeletal muscle $StO_2$, TUT and AUT values could be determined for each location. The difference between cerebral $StO_2$ and flank $StO_2$ may be of great clinical interest. If the aforesaid cerebral/flank $StO_2$ difference reaches a certain physiological threshold, a dangerous clinical condition such as shock may exist, which can cause flank $StO_2$ to decrease a predetermined value below cerebral $StO_2$. A difference AUT value ("DAUT") and a difference TUT value ("DTUT"), representing the difference between each parameter at the two different physical sensor locations (e.g., cerebral and flank), can be determined by a processor 22 as follows:

---
If [(Cerebral StO2 − Flank StO2 value) < difference threshold]
Then
DAUT(present) = DAUT(past) + (Cerebral StO2 − Flank StO2 value − difference threshold) × sample rate.
DTUT(present) = DTUT(past) + sample rate.
   otherwise
DAUT(present) = DAUT(past)
DTUT(present) = DTUT(past)

---

The present invention is not limited evaluating the cerebral and flank regions, and can also be used to evaluate more than two regions.

In some embodiments, the processor 22 may be adapted to determine the converse of AUT and/or TUT values; e.g., the area over threshold ("AOT") and/or the time over threshold ("TOT"). The AOT and/or TOT values could be used in a manner described above to produce clinically significant data. In addition, if a high tissue oxygen saturation threshold has physiological significance, an area over threshold (AOT) value and/or a time over threshold (TOT) value may be of interest.

The following examples are provided as non-limiting examples illustrating the utility of the present invention:

Example 1

In an example of an embodiment of the present method in use, the tissue of a subject is monitored using an apparatus as described herein. The subject is a 90 year old male and is a longtime smoker. The subject's age and smoking status are input into the apparatus by a user (e.g., clinician). Over an interrogation period of several hours, the apparatus interrogates the subject's tissue (e.g., an interrogation rate of 0.5 Hertz) and periodically determines $StO_2$ levels within the subject's cerebral tissue. Based on subject information input by the clinician, the apparatus may automatically select a threshold $StO_2$ value that is acceptable for use with a 90-year-old male smoker. The present apparatus is adapted to periodically (e.g., every 2 seconds) determine one or both of the accumulated AUT and TUT values relative to the threshold. The determined AUT/TUT values may then be displayed on the apparatus. In addition, determined AUT/TUT values may be compared against earlier determined AUT/TUT values to determine trending data and/or rate of change data. If the magnitude of the AUT/TUT values (e.g., the then calculated values, or a difference from the previous values, or the values over a period of time) is great enough, the apparatus may be adapted to provide an indication to the user that a particular type of oxygen desaturation event has occurred or is occurring to alert the user that intervention to restore tissue oxygenation may be necessary.

Example 2

In an example of an embodiment of the present method in use, the subject is a newborn infant. Information about the subject is input into the apparatus by a user, as described above in Example 1. Based on the information input by the user, the present apparatus is adapted to select a threshold $StO_2$ value that is acceptable for use with a newborn infant. The present apparatus periodically measures a TUT value and an AUT value by comparing determined tissue oxygen saturation values and the threshold $StO_2$ value. The apparatus may be adapted to save to memory all of the previously measured TUT and AUT values recorded in time periods in the past, and to monitor changes and trends in the values. For example, in the first six days of the subject's life, the apparatus may record AUT values in the following order: 500, 300, 100, 20, 5, and 0 (arbitrary units). The present apparatus can be adapted to interpret the decreasing trend of the AUT values as an improvement in the subject's physiological state. The apparatus may be adapted to display an indication of the trending improvement.

Example 3

In an example of an embodiment of the present method in use, the tissue of a subject is monitored using the present apparatus. The subject is a 40-year-old male who is undergoing a 5-hour surgery. Subject information is input into the analyzer 12 by the user, in a manner similar to that described above. Based on that information, the present apparatus selects a threshold $StO_2$ value that is acceptable for use with a 40-year-old male. Periodically (e.g., every two seconds) during of the 5-hour surgery, the apparatus updates an AUT value in the manner described above. Each updated AUT value that is generated may be displayed on the display of the apparatus. Based on the accumulated AUT value displayed, the user is able to monitor the health of the subject during the surgery and avoid reaching a physiologically adverse AUT value by intervention to restore tissue oxygen saturation through methods known to increase blood oxygenation (increase inspired O2) and perfusion (increase CO2, give drugs, and/or vasodilators).

Although this invention has been shown and described with respect to the detailed embodiments thereof, it will be understood by those skilled in the art that various changes in form and detail thereof may be made without departing from the spirit and the scope of the invention. For example, the Detailed Description section of the present application describes the analyzer processor 22 as being adapted in various different embodiments to perform defined functions. The functions may alternatively be described as steps within embodiments of the present method.

What is claimed is:

1. A method for monitoring a blood oxygen saturation level within a subject's tissue during a period of time, comprising:
   providing a near infrared spectrophotometric (NIRS) apparatus that includes at least one sensor having at least one light source and at least one light detector, an analyzer having at least one processor, and an input device, wherein the at least one processor is in signal communication with the at least one sensor and the input device;
   applying the at least one sensor to a skin surface of the subject;
   inputting one or more subject characteristics specific to the subject into the processor using the input device;
   using the at least one processor to execute instructions stored in a memory device, which instructions cause the at least one processor to:
      control the at least one light source to emit light into the subject's tissue and to detect the emitted light after the emitted light has passed through the user's tissue using the at least one light detector, wherein the light detector produces signals representative of the detected light;
      periodically determine a value representative of the oxygen saturation level within the tissue based on the signals representative of the detected light;
      determine a threshold oxygen saturation value based on the one or more subject characteristics specific to the subject;
      compare the periodically determined value representative of the oxygen saturation level within the tissue to the determined threshold oxygen saturation value;
      determine a cumulative under threshold value for the period of time using a plurality of the periodically determined values representative of the oxygen saturation level and the determined threshold oxygen saturation value; and
      communicate to a user the cumulative under threshold value.

2. The method of claim 1, wherein the one or more subject characteristics specific to the subject include one or more of the subject's age, weight, height, gender, health, blood pressure, hematocrit, ethnicity, and tobacco usage status.

3. The method of claim 2, wherein the instructions cause the at least one processor to determine the threshold oxygen saturation value using the one or more subject characteristics specific to the subject.

4. The method of claim 1, wherein the cumulative under threshold value for the period of time is a time under threshold (TUT) value.

5. The method of claim 1, wherein the cumulative under threshold value for the period of time is an area under threshold (AUT) value which AUT value is representative of an amount of time under threshold and a magnitude of tissue oxygen deficit during the amount of time under threshold.

6. The method of claim 1, wherein the instructions further cause the at least one processor to determine an under threshold rate of change value based on a plurality of cumulative under threshold values.

7. The method of claim 1, wherein the instructions further cause the at least one processor to determine a trend value based on a plurality of cumulative under threshold values, which trend value is indicative of one of an increase, a decrease, or no change in the cumulative under threshold values over time.

8. An apparatus for monitoring a blood oxygen saturation level within a subject's tissue during a period of time, comprising:
   a near infrared spectrophotometric (NIRS) apparatus that includes at least one sensor having at least one light source and at least one light detector, an analyzer having at least one processor, and an input device, wherein the at least one processor is in signal communication with the at least one sensor and the input device;
   wherein the at least one processor is in communication with a memory device storing instructions, which instructions when executed cause the at least one processor to selectively:
      control the at least one light source to emit light into the subject's tissue and to detect the emitted light after the emitted light has passed through the user's tissue using the at least one light detector, wherein the light detector produces signals representative of the detected light;
      periodically determine a value representative of the oxygen saturation level within the tissue based on the signals representative of the detected light;
      determine a threshold oxygen saturation value based on one or more subject characteristics specific to the subject input into the at least one processor using the input device;
      compare the periodically determined value representative of the oxygen saturation level within the tissue to the determined threshold oxygen saturation value;
      determine a cumulative under threshold value for the period of time using a plurality of the periodically determined values representative of the oxygen saturation level and the determined threshold oxygen saturation value; and
      communicate to a user the cumulative under threshold value.

9. The apparatus of claim 8, wherein the one or more subject characteristics specific to the subject include one or more of the subject's age, weight, height, gender, health, blood pressure, hematocrit, ethnicity, and tobacco usage status.

10. The apparatus of claim 8, wherein the instructions cause the at least one processor to determine the threshold oxygen saturation value using the one or more subject characteristics specific to the subject.

11. The apparatus of claim 8, wherein the cumulative under threshold value for the period of time is a time under threshold (TUT) value.

12. The apparatus of claim 8, wherein the cumulative under threshold value for the period of time is an area under threshold (AUT) value which AUT value is representative of an amount of time under threshold and a magnitude of tissue oxygen deficit during the amount of time under threshold.

13. The apparatus of claim 8, wherein the instructions further cause the at least one processor to determine an under threshold rate of change value based on a plurality of cumulative under threshold values.

14. The apparatus of claim 8, wherein the instructions further cause the at least one processor to determine a trend value based on a plurality of cumulative under threshold values, which trend value is indicative of one of an increase, a decrease, or no change in the cumulative under threshold values over time.

\* \* \* \* \*